(12) United States Patent
Corrigan

(10) Patent No.: US 6,620,952 B1
(45) Date of Patent: Sep. 16, 2003

(54) SYNTHESIS OF POLYOL FATTY ACID POLYESTERS

(75) Inventor: Patrick Joseph Corrigan, Cincinnati, OH (US)

(73) Assignee: The Procter & Gamble Co., Cincinnati, OH (US)

( * ) Notice: Subject to any disclaimer, the term of this patent is extended or adjusted under 35 U.S.C. 154(b) by 0 days.

(21) Appl. No.: 09/889,051

(22) PCT Filed: Jan. 14, 2000

(86) PCT No.: PCT/IB00/00059
§ 371 (c)(1),
(2), (4) Date: Sep. 4, 2001

(87) PCT Pub. No.: WO00/44760
PCT Pub. Date: Aug. 3, 2000

Related U.S. Application Data

(60) Provisional application No. 60/117,614, filed on Jan. 28, 1999.

(51) Int. Cl.[7] .................................................. C11C 3/00
(52) U.S. Cl. ........................ 554/172; 554/169; 554/170; 536/119
(58) Field of Search .............................. 554/169, 170, 554/172; 536/119

(56) References Cited

U.S. PATENT DOCUMENTS

| | | |
|---|---|---|
| 3,963,699 A | 6/1976 | Rizzi et al. |
| 4,517,360 A | 5/1985 | Volpenhein |
| 4,518,772 A | 5/1985 | Volpenhein |
| 5,043,438 A | 8/1991 | Buter |
| 5,158,796 A | 10/1992 | Bernhardt et al. |
| 5,231,199 A | 7/1993 | Willemse |
| 5,767,257 A | 6/1998 | Schafermeyer et al. |
| 5,945,529 A * | 8/1999 | Corrigan et al. ............ 536/119 |
| 6,080,853 A | 6/2000 | Corrigan et al. |

FOREIGN PATENT DOCUMENTS

| | | |
|---|---|---|
| EP | 0 383 404 A2 | 8/1990 |
| WO | WO 92/04360 A1 | 3/1992 |
| WO | WO 98/03526 A1 | 1/1998 |
| WO | WO 98/03527 A1 | 1/1998 |
| WO | WO 98/06731 A1 | 2/1998 |

OTHER PUBLICATIONS

Treybal, Robert E.; "Mass–Transfer Operations", Third Edition; McGraw–Hill Book Company; 1980; Chapter Six; pp. 139–142.

* cited by examiner

Primary Examiner—Deborah D. Carr
(74) Attorney, Agent, or Firm—Carl J. Roof; Erich D. Hemm (57) ABSTRACT

Processes for the synthesis of polyol fatty acid polyester by transesterification of a polyol comprise reacting polyol with a first portion of fatty acid lower alkyl ester to provide a first step reaction product in which substantially all of the polyol is reacted with at least one fatty acid lower alkyl ester. The process then employs a multistage column for further transesterification of the first step reaction product. Partially esterified polyol, a second portion of fatty acid lower alkyl ester and catalyst are fed to the column to form a mixture and cause further transesterification of the partially esterified polyol and fatty acid lower alkyl ester, with lower alkyl alcohol being formed as a by product. The resulting liquid mixture of reactants and product is passed in a first direction between adjacent stages through the column for further reaction of partially esterified polyol with fatty acid lower alkyl ester. An inert sparging gas is fed through the column in a second direction between adjacent stages, counter current to the flow of the liquid mixture between adjacent stages in the first direction. The inert gas is directed through the liquid mixture to provide gas induce turbulence, such that the column reactor has a column ratio of at least 0.4/hour.

19 Claims, 2 Drawing Sheets

SYNTHESIS OF POLYOL FATTY ACID POLYESTERS

This application is a 371 of PCT/IB00/00059 filed Jan. 14, 2000. This application claims the benefit of provisional application Ser. No. 60/117,614 filed Jan. 28, 1999.

FIELD OF THE INVENTION

The present invention is directed to processes for the synthesis of polyol fatty acid polyesters by transesterification of a polyol and using inert gas to remove methanol. More specifically, the present invention is directed to an improved inert gas sparging process employing intense agitation of the fluid in the column to improve mass transfer.

BACKGROUND OF THE INVENTION

Processes for the synthesis of polyol fatty acid polyesters by the transesterification of a polyol are well known in the art. For example, the Rizzi et al. U.S. Pat. No. 3,963,699 discloses a solvent-free transesterification process comprising two main steps, each of which is conducted in a batch reactor. In the first step, a mixture of polyol, a fatty acid lower alkyl ester, an alkali metal fatty acid soap, and a basic catalyst are heated to form a homogenous melt of partially esterified polyol and unreacted starting materials. In a second step, excess fatty acid lower alkyl esters are added to the reaction product of the first step to form the polyol fatty acid polyester. Rizzi et al. further disclose that a lower alcohol is formed as by-product of the reaction and, in order to promote the reaction, the alcohol by-product is preferably removed. Many removal techniques are acknowledged by Rizzi et al. as being known in the art; Rizzi et al. indicate that vacuum removal, both with and without an inert gas, has been found to promote the reaction, and that simple distillation under atmospheric pressure may also be sufficient.

The Volpenhein U.S. Pat. Nos. 4,517,360 and 4,518,772 disclose further solvent-free transesterification processes for producing higher polyol fatty acid polyesters. In U.S. Pat. No. 4,517,360, Volpenhein discloses the use of potassium carbonate, sodium carbonate or barium carbonate as a catalyst and the use of a fatty acid methyl 2-methoxy ethyl or benzyl ester. In U.S. Pat. No. 4,518,772, Volpenhein discloses the use of preferred molar ratios of soap to polyol of from about 0.6:1 to about 1:1 in the first step of the two step process. Volpenhein also employs a batch reaction process and discloses the advantage of removing lower alcohol by-product to promote the transesterification reaction.

The Buter U.S. Pat. No. 5,043,438 discloses a process for the synthesis of polyol fatty acid esters by reacting a polyol and a fatty acid lower alkyl ester under substantially solvent-free conditions. Buter discloses that the process employs a pre-reactor in which the reaction mixture is in steady state with mass-balanced in-going reactant streams and out-going product streams having a polyol conversion of 1% or more, and a nonagitated column main reactor, which in the examples was a three-tray column reactor with counter-current stripping gas, i.e. nitrogen.

U.S. Pat. No. 5,767,257 issued to Schafermeyer et al. discloses a method for producing polyol fatty acid polyesters using atmospheric or superatmospheric pressure, and is incorporated herein by reference. U.S. Pat. No. 5,767,257 teaches that an inert gas can be sparged through a reactor with sufficient mass transfer surface area contact between the inert gas and reactor liquid to transfer lower alkyl alcohol byproducts from the a liquid mixture of the reactants.

Other U.S. Patents related to processes for making polyol polyesters include U.S. Pat. No. 5,231,199 to Willemse, U.S. Pat. No. 5,158,796 to Bernhardt, and U.S. Pat. No. 5,518,772 to Volpenhein.

U.S. Pat. No. 5,945,529, titled "Synthesis of Polyol Fatty Acid Polyesters Using Column with Inert Gas Stripping" to Corrigan et al. and filed on Jul. 19, 1996 discusses the use of inert gas stripping in the synthesis of sucrose polyesters, and is incorporated herein by reference.

Robert E. Treybal, in "Mass-Transfer Operations" Third Edition, 1980 discusses at pages 139–142 discusses sparged vessels, and is incorporated herein by reference.

Removal of lower alkyl alcohol (e.g. methanol) in polyol polyester synthesis is generally desirable to achieve higher degrees of esterification of the polyol. For instance, the equilibrium equation for the synthesis of sucrose octaester from sucrose heptaester and fatty acid methyl ester requires that methanol be removed in order to produce significant quantities of sucrose octaester.

The problems associated with removing lower alkyl alcohol such as methanol is compounded when reactions are to take place on a large scale suitable for commercial application. A vacuum source can be used help extract the methanol, but it is desirable to eliminate the need for vacuum in commercial scale polyol polyester synthesis. Additionally, the static pressure of the liquid reactants in a large scale column reactor tends to compress gas bubbles. The resulting reduction in the surface area of the bubbles results in reduced mass transfer of methanol from the liquid mixture to the stripping gas.

Longer residence times of reactants in the column reactor would generally be expected to increase the transfer of methanol from the liquid mixture of reactants and reaction by-products. However, longer residence times in commercial scale reactors are undesirable from a cost standpoint.

Polyol fatty acid polyesters are increasingly being employed in various applications. Particularly, there has been a significant increase in the use of polyol fatty acid polyesters as low-calorie fats in many food products. Accordingly, the demand for polyol fatty acid polyesters suitable for human consumption is rapidly increasing. As a result, processes for more efficient and economical synthesis of polyol fatty acid polyesters are necessary and desirable. Accordingly, scientists and engineers seek improved methods for removing lower alkyl alcohol from liquid mixtures in the synthesis of polyol polyesters.

SUMMARY OF THE INVENTION

It has now surprisingly been found that inert gas can be employed in commercial scale polyol polyester reaction mixtures to provide the formation of turbulent micro-eddies that significantly enhance mass transfer with the reacting phase. In particular, the gas induced formation of turbulence has been found to be effective in promoting the transfer of methanol from the liquid reaction mixture to the inert gas even under atmospheric and superatmospheric reaction pressures. Moreover, the removal of methanol can be accomplished without long reactor residence times.

According to one aspect of the present invention, a process for the synthesis of polyol fatty acid polyester, such as sucrose octaester, comprises reacting polyol with fatty acid lower alkyl ester to form a liquid mixture comprising polyol polyester, fatty acid lower alkyl ester, and lower alkyl alcohol by-product, while sparging inert gas through the liquid mixture. The inert gas is directed through the liquid mixture at a bulk gas velocity sufficient to provide gas induced turbulent flow of the inert gas through the liquid mixture, wherein the gas induced turbulent flow enhances transfer of the lower alkyl alcohol from the liquid mixture. The reaction of the polyol with fatty acid lower alkyl ester can take place at a reaction pressure of between about 0 and about 15 psig.

The reaction can take place in a multistage column reactor having a column ratio of at least 0.4/hour, preferably at least 0.5/hour, and more preferably at least 0.6/hour. The column ratio is defined as the gas flow rate through the column divided by the mass of reacting liquid present in the column, or:

(Inert Gas Flow Through Column (pounds/hour))

(Mass of Reacting Liquid in the Column (pounds))

The mass of liquid in the column can generally be calculated as the product of the mass flow rate of the reacting liquid in the column multiplied by the residence time of the reacting liquid in the column.

In one embodiment, the present invention provides a two step process for the synthesis of polyol fatty acid polyester. The process comprises a first step of reacting polyol, such as sucrose, with a first portion of fatty acid lower alkyl ester to provide a first step reaction product wherein the polyol is at least about 40% esterified. In a second stage of the process, the first step reaction product and a second portion of fatty acid lower alkyl ester are reacted in a multi-stage column reactor to form a liquid mixture comprising polyol polyester, fatty acid lower alkyl ester, and lower alkyl alcohol by-product. The liquid mixture passes in a first direction through the column reactor while an inert gas, such as nitrogen, is directed in a second direction counter current to the flow of the liquid mixture. The inert gas flow rate is selected relative to the mass of the liquid mixture in the column to provide a column ratio of at least about 0.4/hour, and preferably greater than about 0.5/hour.

In a preferred embodiment, the polyol polyester in the column reaction product is at least about 95% and preferably at least about 97% esterified. The polyol polyester can have a degree of conversion of greater than about 95%, and at least about 60 weight percent, more preferably at least about 70%, and still more preferably at least about 75% of the polyol polyester in the reaction product can be fully esterified polyol polyester (e.g. sucrose octaester when the polyol is sucrose). The column reaction can be conducted with a liquid flow rate of at least about 1800 pounds per hour, preferably at least about 10,000 pounds per hour, wherein the residence of the liquid mixture in the column reactor is less than about 3.0 hours, and more preferably less than about 2.0 hours.

BRIEF DESCRIPTION OF THE DRAWING

The processes of the present invention, and the advantages thereof, will be more fully apparent in view of the accompanying drawing in which.

DETAILED DESCRIPTION

The processes according to the present invention relate to the synthesis of polyol fatty acid polyester by the solvent-less transesterification of polyol. As used herein, the term "polyol" is intended to include any aliphatic or aromatic compound containing at least two free hydroxyl groups. In practicing the processes disclosed herein, the selection of a suitable polyol is simply a matter of choice. For example, suitable polyols may be selected from the following classes: saturated and unsaturated straight and branched chain linear aliphatic; saturated and unsaturated cyclic aliphatic, including heterocyclic aliphatic; or mononuclear or polynuclear aromatics, including heterocyclic aromatics. Carbohydrates and non-toxic glycols are preferred polyols. Monosaccharides suitable for use herein include, for example, mannose, galactose, arabinose, xylose, ribose, apiose, rhamnose, psicose, fructose, sorbose, tagitose, ribulose, xylulose, and erythrulose. Oligosaccharides suitable for use herein include, for example, maltose, kojibiose, nigerose, cellobiose, lactose, melibiose, gentiobiose, turanose, rutinose, trehalose, sucrose and raffinose. Polysaccharides suitable for use herein include, for example, amylose, glycogen, cellulose, chitin, inulin, agarose, zylans, mannan and galactans. Although sugar alcohols are not carbohydrates in a strict sense, the naturally occurring sugar alcohols are so closely related to the carbohydrates that they are also preferred for use herein. The sugar alcohols most widely distributed in nature and suitable for use herein are sorbitol, mannitol and galactitol.

Particularly preferred classes of materials suitable for use herein include the monosaccharides, the disaccharides and sugar alcohols. Preferred carbohydrates and sugar alcohols include xylitol, sorbitol and sucrose. Sugar ethers and alkoxylated polyols, such as polyethoxy glycerol can also be used herein.

The fatty acid lower alkyl esters which are employed as reactants in the present processes include the methyl and ethyl esters of fatty acids containing about eight or more carbon atoms, and preferably containing from 8 to about 22 carbon atoms, and mixtures of such esters. Suitable esters can be prepared by the reaction of diazoalkanes and fatty acids, or derived by alcoholysis from the fatty acids naturally occurring in fats and oils. Fatty acid esters suitable for use herein may be derived from either saturated or unsaturated fatty acids. Suitable preferred saturated fatty acids include, for example, capric, lauric, palmitic, stearic, behenic, isomyristic, isomargaric, myristic, caprylic, and anteisoarachadic. Suitable preferred unsaturated fatty acids include, for example, maleic, linoleic, licanic, oleic, linolenic, and erydiogenic acids. Mixtures of fatty acids derived from soybean oil, palm oil, coconut oil, cottonseed and fatty hydrogenated rapeseed oil are especially preferred for use herein. Methyl esters are the preferred fatty acid esters for use herein, since their use in the processes herein tends to result in high yields of polyol fatty acid polyesters.

A catalyst is preferably employed in the processes of the present invention. The catalyst may be any one of a number of basic catalysts known in the art for use in the transesterification of polyol. Preferably, the catalyst is selected from the group consisting of alkali metals, including sodium, lithium or potassium, other metals such as calcium or aluminum, alloys of two or more of these metals, or compounds of these metals, including but not limited to, carbonates, bicarbonates, alkoxides, or hydroxides of these metals, or mixtures thereof In a further preferred embodiment of the present processes, the basic catalyst is a carbonate, bicarbonate, alkoxide or hydride of sodium or potassium, or comprises mixtures of two or more of these compounds. Preferably, the catalyst is employed both in the initial reaction of the polyol with the first portion of fatty acid lower alkyl ester, and in the subsequent reaction of the first step reaction product of partially esterified polyol with the second portion of the fatty acid lower alkyl ester which is conducted in the multistage column.

The initial reaction of the polyol and the first portion of the fatty acid lower alkyl ester may be conducted in accordance with procedures known in the art, for example as employed in the first steps of the methods taught in the Rizzi et al. U.S. Pat. No. 3,963,699 and the Volpenhein U.S. Pat. Nos. 4,517,360 and 4,518,772, all of which are incorporated herein by reference. The amounts of polyol and fatty acid lower alkyl ester reactants, catalyst and emulsifier, if employed, used in the initial transesterification reaction of polyol with the first portion of the fatty acid lower alkyl ester may be those conventionally employed by Rizzi et al, Volpenhein and others in the art. In preferred embodiments, the initial reaction of polyol and the first portion of fatty acid alkyl ester employs a polyol:fatty acid lower alkyl ester molar ratio of from about 1:3 to about 1:7, with a ratio of about 1:5 being particularly preferred. The molar ratio of polyol to catalyst is preferably in the range of from about 1:0.01 to about 1:0.5, with a molar ratio of about 1:0.1 being preferred.

As is well known in the art, the initial reaction of the polyol with the first portion of the fatty acid lower alkyl ester may be conducted in the presence of an emulsifier. The emulsifier assists in overcoming the incompatibility of the polyol and the fatty acid lower alkyl ester reactants which is a result of the heterogeneous nature of the reactants. Suitable emulsifiers include alkali metal fatty acid soaps, including alkli metal salts of saturated and unsaturated fatty acids having at least about 8 carbon atoms, and preferably from about 8 to about 18 carbon atoms. Accordingly, suitable alkali metal fatty acid soaps include, but are not limited to, the lithium, sodium, potassium, rubidium and cesium salts of fatty acids such as capric, lauric, myristic, palmitic, licanic, parinaric and stearic acids. Mixtures of fatty acids derived from soybean oil, sunflower oil, safflower oil and corn oil are preferred for use in the alkali metal soaps. Alternatively, or in addition to the alkali metal soaps, partially esterified polyol may be employed to solubilize the polyol and thereby transfer the polyol into a liquid phase together with the fatty acid lower alkyl ester reactant. The emulsifier is preferably used in an amount sufficient to provide a polyol:emulsifier molar ratio in a range of from about 1:0.01 to about 1:1.

The reaction is conducted until substantially all of the polyol is reacted with at least one fatty acid lower alkyl ester, i.e. at least one hydroxy group on substantially all of the polyol molecules has been esterified. Preferably, the reaction product of this initial or fist step of the reaction contains less than about 2 weight percent of unreacted polyol, i.e., polyol in which none of the hydroxy groups are esterified, and more preferably less than about 1 weight percent of unreacted polyol, and most preferably less than about 0.5%. The reaction product of this first step will typically comprise lower ester products. The degree of conversion of the polyol, i.e., the percentage of polyol hydroxyl groups converted to ester groups, in the first step reaction product is preferably in the range of from about 15 to about 60 percent, and more preferably is at least about 25 percent, and more preferably is about 50 percent.

Lower alkyl alcohol by-product from the initial transesterification reaction should be removed to increase the rate of reaction. While the reaction will proceed to a certain limited extent if the alcohol by-product remains in the reaction mixture at this state, the reaction rate is lower. In a preferred embodiment, the lower alkyl alcohol by-product is removed, for example by conducting the initial reaction under vacuum or by providing inert gas sparging or stripping in the reactor.

Preferably, the initial reaction of the polyol and the first portion of the fatty acid lower alkyl ester is conducted in any type of reactor which allows some back mixing of product with reactants. Back mixing of partially esterified polyol product with the polyol reaction allows solubilization of the polyol reactant, and the faster the polyol is transferred to the liquid phase where it is available for reaction with the fatty acid lower alkyl ester, the faster this stage of the reaction will proceed to completion.

To obtain the desirable back mixing, the initial transesterification may be conducted in a semi-batch manner in a batch type reactor as employed by Rizzi et al. and others. Alternatively, the initial transesterification may be conducted in one or more continuous stirred tank reactors arranged in series. Preferably, one or two continuous stirred tank reactors are employed for this initial reaction. When two continuous stirred tank reactors are employed, it is preferred that the output product from the first reactor contains not greater than about 5 weight percent, and more preferably not greater than about 2 weight percent, unreacted polyol.

In a further alternative embodiment, the initial transesterification may be conducted in a multistage column reactor which allows some back mixing between reactants and product. The multistage column reactor may be separate from or form a part of the multistage column reactor employed in the subsequent step of the present processes. When a multistage column providing back mixing is employed for the initial reaction of polyol, from about two to about six stages of a multistage column are particularly suitable for conducting the initial transesterification reaction of polyol and the first portion of fatty acid lower alkyl ester. One of ordinary skill in the art will recognize that if a column reactor is employed for the initial transesterification reaction, one or more steps must be taken to prevent solid polyol reactant from interfering with operation of the column. For example, solid polyol reactant may be emulsified and/or solubilized with partially esterified polyol prior to introduction of the polyol into the column. Alternatively, the first stage of the column into which the polyol is introduced can be provided with filter means or the like which prevent solid material from being transferred to a subsequent stage of the column.

In accordance with one embodiment of the present invention, the first step reaction product is then provided, together with a second portion of fatty acid lower alkyl ester, to a multistage column reactor for further transesterification. As discussed above, it is well known in the art that the transesterification reaction of the polyol with a fatty acid lower alkyl ester results in the formation not only of the polyol fatty acid polyester, but also in the formation of a lower alkyl alcohol by-product. When fatty acid methyl esters are employed as reactants, the lower alkyl alcohol by-product comprises methanol. It is also well known in the art that removal of the lower alkyl alcohol by-product such as methanol promotes further transesterification reaction, particularly in the later stages of reaction as the higher esters of a polyol such as sucrose are produced. In the present processes, improved removal of the lower alkyl alcohol during the transesterification reaction is achieved.

More particularly, the synthesis of the polyol fatty acid polyester product from the first step reaction product is effected in a multistage column with inert gas sparging. The column is operated to provide a column ratio of at least about 0.4/hour, more preferably at least about 0.5/hour, and still more preferably at least about 0.6/hour.

It is been found that there is a minimum superficial gas velocity that should be present in order to provide enough gas-induced agitation in the column reactor to achieve high conversions of the polyol (e.g. in the case of sucrose, at least about 60%, more preferably at least about 75% or more of the sucrose is fully esterified to sucrose octaester, corresponding to about 95% esterification of available hydroxyl sites). Superficial gas velocity is the speed with which the bulk of the inert sparging gas, on average, travels through the column reactor. While higher gas velocities through the column might be considered detrimental in that higher gas velocities result in shorter residence time of the gas in the column, and shorter time for transfer of methanol from the liquid mixture in the column to the inert gas, it has been found that faster superficial gas velocities through the column provide enough gas induced agitation such that increased, rather than decreased conversion to sucrose octaester is achieved.

In terms of column reactor design, the column ratio defined above provides a ratio of inert gas flow rate through the column to the mass of liquid in the column. It has been found that for a given column size, the inert gas velocity through the column should be selected to provide a column ratio of at least about 0.4/hour, preferably at least about 0.5/hour, and still more preferably at least about 0.6/hour. Accordingly, the present invention permits relatively high conversion of polyol to polyol polyester (e.g. sucrose to sucrose octaester), regardless of the scale of the reactor.

Figure 1:
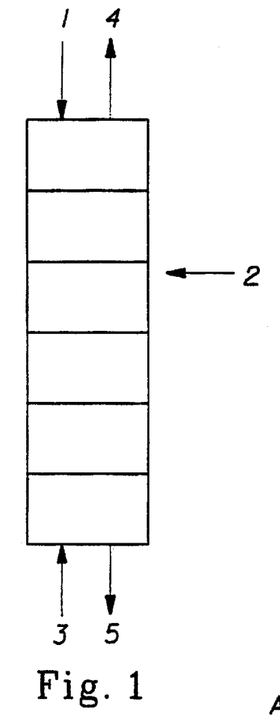
FIG. 1 is a schematic diagram of one embodiment of a multistage column suitable for use according to the present invention.

A schematic diagram of a suitable multistage column is shown in FIG. 1. As demonstrated in FIG. 1, the first step reaction product comprising partially esterified polyol and a second portion of fatty acid ester reactant are fed to the column, together with the catalyst, shown schematically by arrow 1. The reactants for the further transesterification reaction may be provided to the column individually or separately, and then mixed therein, or alternatively, the reactants may be supplied together in one or more common inlet streams. The entire amount of the fatty acid lower alkyl ester for the remainder of the transesterification reaction may be fed directly into the first stage of the column, together with the partially esterified polyol first step reaction product and the catalyst. Alternatively, a third portion of the fatty acid lower alkyl ester may be fed into the column at one or more stages which are intermediate to the ends of the column, shown schematically in FIG. 1 by arrow 2, thereby providing additional ester reactant for reaction with partially esterified polyol which is intermediate the ends of the column. The second and any additional portions of fatty acid alkyl ester which are added to the column are provided in an amount which, combined with the first portion of fatty acid alkyl ester employed in the initial stage, provides a total molar ratio of ester groups to polyol hydroxyl groups of greater than 1. When the polyol comprises sucrose and the fatty acid alkyl ester is a monoester, the molar ratio of total ester to sucrose is preferably at least 10:1.

Similarly, the catalyst may be supplied separately to the column, or alternatively, the catalyst may be combined with one or both of the partially esterified polyol and fatty acid ester reactants prior to their introduction into the column.

The inert gas is also fed through the column, preferably to a location remote from the reactants' inlets. For example, as shown schematically by arrow 3 in FIG. 1, the inert gas is preferably fed to the end of the column opposite that to which the reactants and catalysts are supplied, thereby providing counter-current flow between the inert gas and liquids within the column. As further shown schematically by arrow 4 in FIG. 1, the inert gas containing the alcohol by-product resulting from reaction of the partially esterified polyol and fatty acid lower alkyl ester is removed from the column, separate from removal of the liquid polyol polyester reaction product shown in FIG. 1 by arrow 5. While concurrent flow between the inert gas and liquids in the column may be employed, counter-current flow is preferred as it provides increased efficiency in removal of the lower alkyl alcohol by-product.

For purposes of illustration only, the column shown in FIG. 1 has six segments or stages. In practice, the number of stages can be varied depending on the specific reactants, catalysts, reaction conditions and degree of conversion desired for the polyol polyester product. In practice a column having from 3 to about 18 segments or stages, preferably about four to six stages, is suitable for production of higher polyol fatty acid polyesters.

Figure 2:
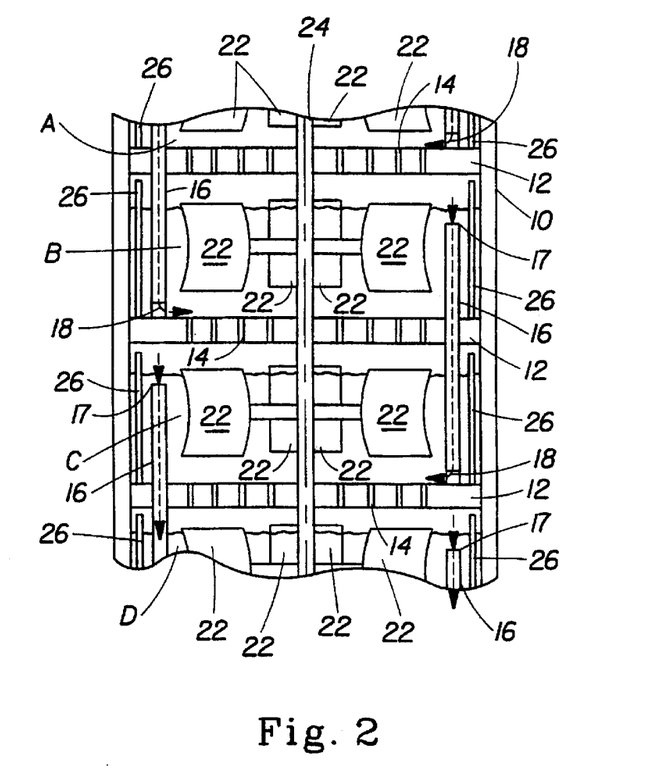
FIG. 2 is a schematic cross-sectional diagram of a portion of a multistage column suitable for use according to the present invention.

In the multistage column employed in the present processes, each segment or stage can be separated from an adjacent prior stage by a segment plate, and each segment plate can be provided with at least one passage allowing transfer of a liquid in a first direction between adjacent stages and with at least one passage allowing transfer of a gas in a second direction between adjacent stages, with the second direction being counter current to the first direction. While not required, it is preferred that the passages prevent transfer of solids between adjacent stages. One embodiment of a multistage column suitable for use in the present processes is shown in schematic cross section in FIG. 2. With reference to FIG. 2, the illustrated portion of the column 10 is shown having a plurality of stages A, B, C, D. The respective stages are separated from one another by a segment plate 12. In the embodiment of FIG. 2, each segment plate is provided with perforations or sieve holes 14 which allow the upward passage of the inert gas therethrough and provide for transfer of gas between adjacent stages. The pressure and/or flow rate of the inert gas moving through the column prevents transfer of liquids or solids between adjacent stages through the sieve holes 14.

The passage allowing transfer of liquid between adjacent stages of the multistage column shown in FIG. 2 comprises a series of overflow/downcomer tubes 16 provided with inlets 17 and outlets 18. More specifically, as the liquid in one stage reaches the height at which the inlet 17 of the overflow portion of the tube 16 is positioned, liquid flows through the overflow portion of the tube 16 down through the segment plate to the downcomer portion of tube 16 which is provided with an outlet 18 in the adjacent stage. The overflow tubes 16 may be provided with a filter screen or the like at their inlet 17 in order to prevent any solids, for example undissolved polyol, from passing therethrough. As shown in FIG. 2, the outlet 18 of the downcomer tube is preferably positioned in the lower area of the stage, thereby increasing the time for liquid-gas contact occurring within each stage as liquid flows upwardly in each stage to the overflow tube inlet. As also illustrated in FIG. 2, it is preferred that the overflow/downcomer tubes of adjacent stages are positioned remote from one another, thereby increasing the distance between the downcomer outlet 18 and the overflow inlet 17 in a particular stage. This arrangement contributes to increase gas-liquid contact in the column. The overflow/downcomer tubes may be located internal or external to the column.

As will be appreciated, the size of the sieve holes 14, the number of sieve holes 14 and the pattern of sieve holes 14 may be varied depending on the desired inert gas flow between adjacent stages. Similarly, the height of the overflow portion of tubes 16, the length of the downcomer portion of tubes 16 and the shape and position of the overflow/downcomer tubes 16 may also be varied within the scope of the present processes.

In an alternate embodiment to that shown in FIG. 2, each segment plate may be provided with restrictive holes. The column may be operated to limit the flow of gas in one direction and liquid in the opposite direction while permitting the flow of liquid in the one direction and the flow of gas in the opposite direction. Additional passages allowing transfer of a liquid in a first direction and gas in a second direction between adjacent stages, are known in the art and suitable for use in the multistage column employed in the present processes.

In a preferred embodiment of the present processes, the first step reaction product of partially esterified polyol, the second portion of fatty acid lower alkyl ester and catalyst are fed to one end of the column to form a mixture and cause further transesterification of the partially esterified polyol with fatty acid lower alkyl ester, with lower alkyl alcohol being formed as a by-product. The resulting liquid mixture of reactants and product are then passed in the first direction (downwardly in the embodiment of FIG. 2) between adjacent stages through the column, whereby further reaction of partially esterified polyol with fatty acid lower alkyl ester occurs. Nitrogen sparging gas is fed through the column in the second direction (upwardly in the embodiment of FIG. 2) between adjacent stages, with radial shear agitation in each stage, and counter current to the flow of the liquid mixture between adjacent stages in the first direction. Lower alkyl alcohol by-product resulting from the polyol fatty acid lower alkyl ester reaction is transferred from the liquid mixture to the inert gas. Removal of the lower alkyl alcohol by-product promotes further reaction of partially esterified polyol with fatty acid lower alkyl ester.

Any inert gas having a suitable partial pressure sufficient to affect transfer of the lower alkyl alcohol from the liquid phase to the gas phase may be employed. Suitable inert gases include nitrogen, carbon dioxide, superheated, vaporized alkanes, or any of the noble gases (Ne, Xe, etc.). Particularly preferred inert gases for use in the processes of the present invention include nitrogen and aliphatic hydrocarbons, for example, hexane.

In order to maximize the gas-liquid contact surface area, and in turn maximize mass transfer of the lower alkyl alcohol by-product from the liquid reactant-product mixture to the inert gas, the inert gas can additionally be provided with mechanical agitation creating radial shear within one or more stages, preferable every stage, of the column. The combination of plug flow within the column and the radial shear agitation reduces the size of the inert gas bubbles within the liquid mixture and provides increased gas-liquid contact of the stripping gas and the liquid mixture containing the alcohol by-product. As a result, the amount of alcohol by-product transferred to the inert gas is increased. Specifically, the partial pressure of the lower alkyl alcohol by-product, i.e. methanol, is reduced according to the present processes, thereby promoting transfer of the alcohol from the liquid mixture to the inert gas. Preferably, the partial pressure of the alcohol, i.e., methanol, in the final stage of the multistage column is reduced to less than about 10 mm Hg, more preferably less than about 5 mm Hg, and most preferably less than about 2 mm Hg, by the incoming inert gas. The mechanical agitation can aid in reducing the amount of nitrogen gas necessary to promote the reaction to the desired degree of completion, as compared with processes employing a series of continuous stirred tank reactors or a column without radial shear agitation. Suitable weight ratios of inert gas to liquid reactant feed to the column are in the range of less than about 4:1, preferably less than about 3:1, more preferably less than about 2.5:1, and most preferably not greater than about 2:1.

The column is preferably provided with at least one agitator in each stage of the column. More preferably, each stage of the column is provided with at least one agitator providing radial shear to increase contact surface area between the liquid mixture and the inert gas. It is also preferred that axial shear within each segment or stage of the column is minimized. The agitators in each segment or stage of the column therefore serve to disperse the inert gas into the liquid mixture and provide radial mixing. This reduces the average size of inert gas bubbles in the liquid, preferably to less than about 5 mm in diameter, more preferably to less than or equal to about 2 mm in diameter, and increases the amount of gas-liquid contact surface area which in turn, increases the efficiency of the mass transfer of the lower alkyl alcohol from the liquid mixture to the inert gas.

The agitation means is preferably in the form of impeller blades which are parallel to a drive shaft extending axially along the column. In the embodiment of the multistage column shown in FIG. 2, each segment or stage is provided with a plurality of impeller or agitator blades 22 which are arranged around a central axis 24. The central axis 24 rotates the agitator blades 22 to increase radial shear and consequently increase the contact surface area between the liquid reactant-product mixture and the inert sparging gas. The agitator or impeller blades may be curved or flat. The agitator blades 22 shown in the embodiment of FIG. 2 are curved in order to provide a lower aeration number. In a preferred embodiment, the agitator blades are concave in the direction of agitation, i.e. rotation. The radial shear agitation preferably results in an aeration number of less than about 2.0, and more preferably less than about 1.0, where aeration number (Ae) is calculated as (inert gas volumetric flow rate)/(agitator speed)/(agitator diameter)$^3$. As will be appreciated, the number of blades per stage, the dimension and orientation of the blade surfaces and the position of the blades within each segment may be varied in order to increase radial shear within the stage and increase the surface area contact between the liquid mixture and the inert gas in each segment or stage of the column. Preferably, from about 4 to about 20 agitator blades are provided in each stage, more preferably from about 6 to about 12 agitator blades are provided in each stage.

In order to further increase the gas dispersion in the liquid mixture, one or more segments or stages of the multistage column can be provided with one or more baffles extending between adjacent segment plates. Preferably each segment or stage of the multistage column is provided with a plurality of vertical baffles extending between adjacent segment plates defining the respective stage, with the baffles providing increased contact surface area between the liquid mixture and the inert gas within the stage. For example, in the embodiment of FIG. 2, a series of vertical baffles 26 are provided in each stage extending between adjacent segment plates. The baffles 26 are arranged near the outer perimeter of the segment plates. The combination of the vertical baffles and the blade agitators are particularly advantageous for providing increased radial shear of the inert gas in the liquid mixture and improving the transfer of the lower alkyl alcohol from the liquid mixture to the inert gas, thereby promoting the transesterification reaction.

The residence time for the reaction material in the multistage column according to the present processes is reduced as compared with conventional processes, thereby contributing to the efficiency of the present processes. Although residence time for the reaction materials will vary depending on the specific reactants and reactor parameters and conditions, in preferred embodiments of the present processes, particularly wherein the polyol is sucrose, residence times of less than about three hours are possible, and are preferably less than about two hours.

In order to affect and promote the transesterification reactions, both in the original transesterification of polyol and in the further transesterification in the multistage column, heat is preferably supplied to the reactions so that the reactions can be conducted at an elevated temperature in the range of from about 110 C. to about 180 C., more preferably from about 120 C. to about 150 C. In one embodiment, this elevated temperature can be provided by heating the contents of the respective reactors in situ. Alternatively, or in addition, one or more of the feed streams to the respective reactors may be preheated whereby polyol, fatty acid lower alkyl ester, partially esterified polyol and/or the inert gas are preheated to a temperature in the range of from about 120 C. to about 150 C. Heating can also be accomplished by providing sufficient power to the agitator drive to heat the liquid by frictional energy as it is agitated.

In conventional processes for the transesterification of polyol, the reactions have been conducted under vacuum conditions in order to facilitate removal of the lower alkyl alcohol by-product from the liquid polyol polyester product. As discussed above, the initial transesterification of polyol may similarly be conducted under vacuum. Additionally, while the further transesterification conducted in the multistage column according to the present process may similarly be conducted under vacuum conditions, the use of the multistage column and the present process steps allow the further transesterification reaction in the multistage column to be affected at atmospheric or super atmospheric pressures while maintaining the ability to remove the alcohol from the liquid product by use of the inert gas sparging stream provided with radial shear agitation. In fact, employment of atmospheric and super atmospheric pressures, rather than the vacuum conditions, in the multistage column are preferred for use in the present processes in order that the lower alkyl alcohol by-product may be more efficiently removed and recovered from the inert gas during later processing of the inert gas. As a result, recycle and reuse of the inert gas is facilitated. Accordingly, for conducting the presents methods, the reaction pressure in the column (pressure at the top of the column) is preferably in the range of from about 760 mm Hg to about 2500 mm Hg, more preferably from about 760 mm Hg to about 1100 mm Hg. In one embodiment, the pressure at the top of the column can be between about 0 psig and about 15 psig. One of ordinary skill in the art will recognize that the pressure at the bottom of the column will therefore be higher owing to the height of the column, liquid levels and changes in pressure resulting therefrom.

An additional advantage provided by the present processes employing a multistage column provided with agitation is that higher viscosity liquids can be utilized therein while still obtaining the desired gas-liquid contact and transfer of lower alkyl alcohol from liquid to inert gas. This is an especially important advantage in the production of sucrose fatty acid polyesters.

The processes of the present invention are particularly advantageous for producing polyol fatty acid polyester of a high degree of conversion. For example, the processes of the present invention may be used to affect at least 80%, more preferably greater than 90%, and in many cases greater than 95%, conversion of the hydroxyl groups of the polyol to ester groups. In a preferred embodiment of the invention, wherein the polyol is sucrose, the sucrose polyester product has a degree of conversion of greater than 95%, with at least 60 weight percent of the sucrose polyester product, more preferably at least 70 weight percent of the sucrose polyester product, and still more preferably at least about 75 weight percent of the sucrose polyester product comprising sucrose octaester. Optionally, partially esterified polyol product which is removed from the column in the desired product may be separated from the fully esterified product and recycled to the first stage or an intermediate stage of the column for further reaction with additional fatty acid lower alkyl ester reactant.

In accordance with conventional processes, the polyol fatty acid polyester product of the present processes may be subjected to washing, drying, bleaching, filtration, separation and/or deodorization processing steps and/or blended with other components for providing a final product.

In a further embodiment of the processes of the present invention, the inert gas containing the lower alkyl alcohol by-product is removed from the column and further processed to remove substantially all of the lower alkyl alcohol from the inert gas. Removal of substantially all of the lower alkyl alcohol from the inert gas requires that the partial pressure of the lower alcohol in the inert gas be reduced to less then about 10 mm Hg, preferably less than about 5 mm Hg, and most preferably less than about 2 mm Hg after this step. The inert gas with substantially all of the lower alkyl alcohol removed therefrom may then be recycled to the column. The lower alkyl alcohol may be removed from the inert gas using any of the conventional techniques known in the art. For example, the lower alkyl alcohol may be removed from the inert gas by cooling the inert gas which contains the alcohol, and passing the cooled product through an absorbent material, for example, carbon black, or the like, to absorb the alcohol from the gas.

The following examples are set forth to illustrate various features of the present processes. In the examples and the remainder of the present specification, parts and percentages are by weight unless otherwise specified.

EXAMPLES

The following examples illustrate polyol conversion reactions at various scales (3 inch, 6 inch, 12 inch, 4 foot, and 9 foot column diameters), with various liquid and inert gas flow rates. Table 1, below, summarizes the examples.

In each example, the reaction is run in two steps. The first step is carried out in two continuous stirred tank reactors (CSTR's) arranged in series. In the first step, about 9 moles of fatty acid methyl ester, about 0.1 moles potassium carbonate catalyst, and about 0.15 moles potassium soap are added to the reactor for each mole of sucrose added. The reaction is run under vacuum, at 135 C. for 3–4 hours until the reaction mixture is about 50% esterified.

An additional 2 moles of fatty acid methyl ester per mole of sucrose are added to the reaction mixture at the end of the first step, at which point the reaction mixture is directed to a column reactor having mechanical agitation as described above.

In the second step, the material from the first step is pumped continuously into the top of a multistage column reactor. The liquid moves downward through the column and exits at the bottom.

Nitrogen gas is pumped into the bottom of the column, rises through the liquid, and exits through the top. As it rises through the liquid, it vigorously agitates the liquid on a micro-scale, and simultaneously removes methanol by-product. The column is run at a pressure of about 0–15 psig, a temperature of about 135 C. and a residence time of 1–3 hours.

TABLE 1

| Column Diameter | Liquid Flow Rate through the Column (lb/hr) | Gas Flow Rate through the Column (lb/hr) | Residence Time of the Liquid in the Column (hr) | Mass of Liquid in Column | % Sucrose Octaester in the Column Product | Column Ratio (l/hr) |
|---|---|---|---|---|---|---|
| (1) 3" | 2.6 | 2.6 | 1.5 | 3.97 | 75 | 0.667 |
| (2) 3" | 2.0 | 2.0 | 2.0 | 3.97 | 61.6 | 0.500 |
| (3) 3" | 1.3 | 1.3 | 3.0 | 3.97 | 28.6 | 0.333 |
| (4) 6" | 5.3 | 5.3 | 3.8 | 19.8 | 57 | 0.267 |
| (5) 6" | 5.3 | 7.9 | 3.8 | 19.8 | 66 | 0.400 |
| (6) 6" | 5.3 | 10.6 | 3.8 | 19.8 | 75 | 0.533 |
| (7) 6" | 14.5 | 15.9 | 1.4 | 19.8 | 75 | 0.800 |
| (8) 12" | 29.8 | 52.0 | 2.0 | 60.5 | 81 | 0.860 |
| (9) 12" | 28.1 | 52.0 | 2.1 | 58.4 | 74 | 0.890 |
| (10) 12" | 30.2 | 30.0 | 2.1 | 62.5 | 44 | 0.480 |
| (11) 12" | 58.0 | 81.2 | 2.4 | 139.2 | 75 | 0.583 |
| (12) 12" | 53.0 | 100.7 | 3.0 | 160.6 | 88 | 0.627 |
| (13) 4' | 2700.0 | 5400.0 | 1.7 | 4698.0 | 81 | 1.149 |
| (14) 4' | 1890.0 | 5386.5 | 2.2 | 4195.8 | 75 | 1.284 |
| (15) 9' | 22400.0 | 26900.0 | 1.8 | 40320.0 | 76 | 0.667 |

Examples 1–3 are rum with a 3 inch column, examples 4–7 with a 6 inch column, examples 8–12 with a 12 inch diameter column, examples 13–14 with a 4 foot column, and example 15 is run with a 9 foot diameter column. The examples in Table 1 are graphically illustrated in FIG. 3. Examples 1–2 and 5–15 exhibit column ratios of at least 0.4/hour, while examples 3 and 4 have column ratios less than 0.4/hour.

Figure 3:
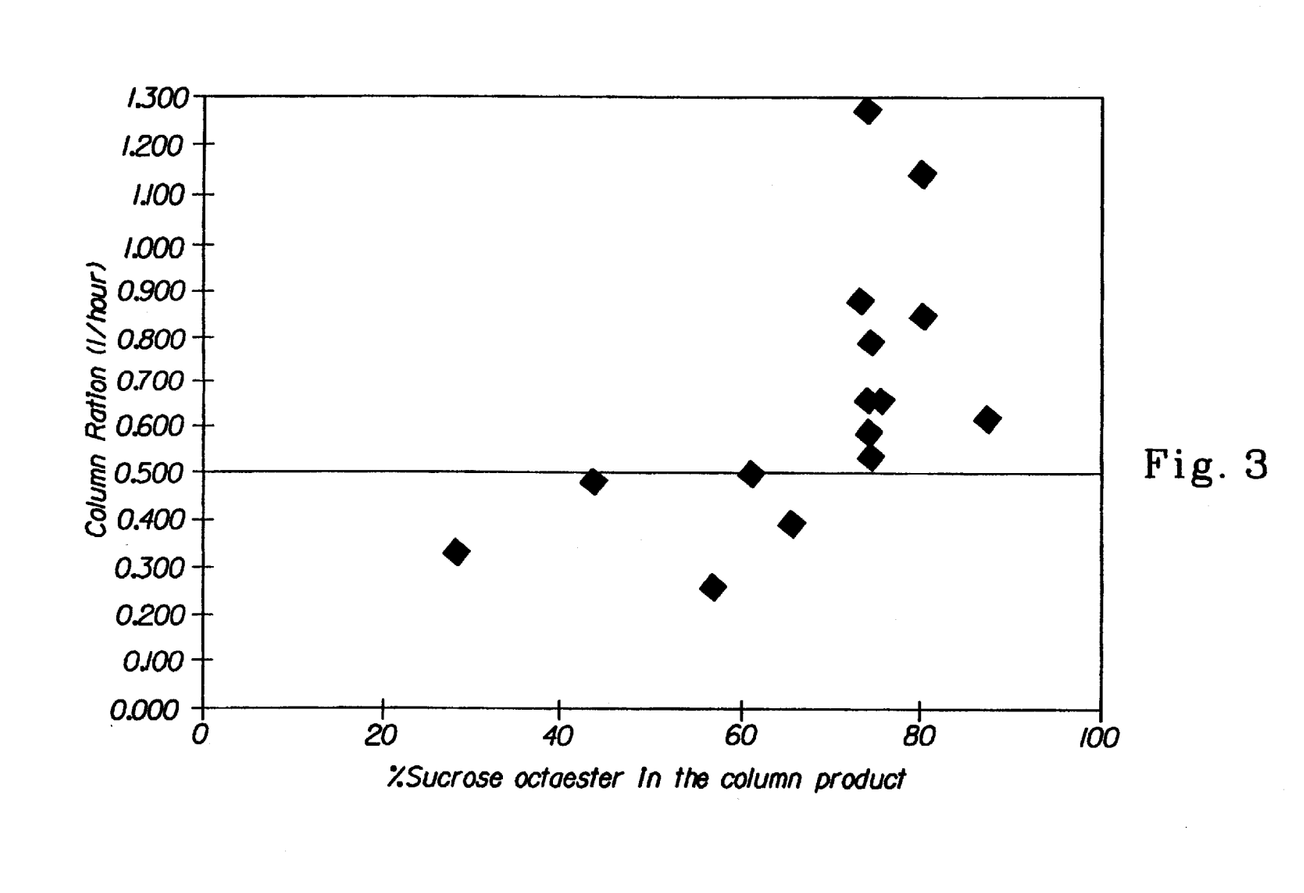
FIG. 3 is a graphical illustration of the data in Table 1, below, depicting the percentage of esterified sucrose which is octaester on the X-axis, and column ratio on the Y-axis.

It can be seen from Table 1 and FIG. 3 that relatively high levels of sucrose octaester can be achieved when the column ratio is greater than about 0.4. For column ratios greater than about 0.5, the sucrose polyester in the reaction product is greater than about 60% octaester, regardless of scale. This ratio can therefore be advantageously used when designing a column reactor.

Moreover, Table 1 and FIG. 3 illustrate that, contrary to what one might expect, increased residence time of the liquid in the column reactor does not necessarily result in improved octaester content. For example, the three examples for the 3 inch column listed in Table 1 illustrate that for a one to one ratio of gas flow rate to liquid flow rate, the percentage sucrose octaester in the column product increases with column ratio and decreases with residence time of the liquid in the column.

The specific and preferred embodiments provided herein are set forth to illustrate the invention and are not intended to limit the scope of the methods of the present invention. Additional embodiments and advantages within the scope of the claimed invention will be apparent to one of ordinary skill in the art.

What is claimed is:

1. A process for the synthesis of polyol fatty acid polyester by transesterification of polyol, comprising reacting polyol with fatty acid lower alkyl ester in a column reactor to form a liquid mixture comprising polyol polyester, fatty acid lower alkyl ester and lower alkyl alcohol by-product; and sparging an inert gas through the liquid mixture at a bulk gas velocity sufficient to provide a column ratio of at least about 0.4/hour.

2. The process of claim 1 wherein the step of reacting polyol with fatty acid lower alkyl ester is conducted at a reaction pressure of at least atmospheric pressure.

3. The process of claim 2 wherein the reaction pressure is between about 0 and about 15 psig.

4. The process of claim 1 wherein the step of reacting polyol with fatty acid lower alkyl ester is a continuous reaction process.

5. The process of claim 2 wherein the step of reacting polyol results in at least about 95% esterification of the polyol.

6. The process of claim 5 wherein the step of reacting polyol results in at least about 97% esterification of the polyol.

7. The process of claim 1 wherein the column ratio is at least 0.5/hour.

8. The process of claim 7 wherein the reaction has a liquid mixture flow rate of at least about 1800 pounds per hour.

9. The process of claim 8 wherein the reaction has a liquid mixture flow rate of at least about 10,000 pounds per hour.

10. The process of claim 9 wherein the column ratio is at least about 0.6/hour.

11. A process for the synthesis of polyol fatty acid polyester by transesterification of polyol, comprising reacting polyol with a first portion of fatty acid lower alkyl ester to provide a first step reaction product wherein the polyol is at least about 40% esterified;

providing a multistage column reactor;

providing the first step reaction product and a second portion of fatty acid lower alkyl ester to the column reactor to cause reaction of the first step reaction product and fatty acid lower alkyl ester and form a liquid mixture comprising polyol polyester, fatty acid lower alkyl ester and lower alkyl alcohol by-product;

passing the liquid mixture in a first direction between adjacent stages through the column reactor; and directing an inert gas through the column in the second direction between adjacent stages, counter current to the flow of the liquid mixture in the first direction, wherein the inert gas is directed through the column to provide a column ratio of at least about 0.4/hour.

12. The method of claim 11 comprising directing the inert gas through the column to provide a column ratio of at least about 0.5/hour.

13. The method of claim 12 comprising directing the inert gas through the column to provide a column ratio of at least about 0.6/hour.

14. The process of claim 11 wherein the polyol in the column reaction product is at least about 95% esterified.

15. The process of claim 11 wherein the column reaction has a liquid mixture flow rate of at least about 1800 pounds per hour.

16. The process of claim 15 wherein the residence time of the liquid mixture in the column reactor is less than about 3.0 hours.

17. The process of claim 15 wherein the reaction has a liquid mixture flow rate of at least about 10,000 pounds per hour.

18. The process of claim 17 wherein the residence time of the liquid mixture in the column reactor is less than about 2.0 hours.

19. A process for the synthesis of sucrose polyester by transesterification of sucrose, comprising reacting sucrose with a first portion of fatty acid lower alkyl ester to provide a first step reaction product;

providing a multistage column;

providing the first step reaction product and a second portion of fatty acid lower alkyl ester to the column reactor to cause reaction of the first step reaction product and fatty acid lower alkyl ester and form a liquid mixture comprising sucrose polyester, fatty acid lower alkyl ester and lower alkyl alcohol by-product;

passing the liquid mixture in a first direction between adjacent stages through the column reactor, wherein the liquid flow rate through the column is at least about 10,000 pounds per hour; and directing an inert gas through the column in the second direction between adjacent stages, counter current to the flow of the liquid mixture in the first direction, wherein the inert gas is directed through the column to provide a column ratio greater than about 0.6/hour;

wherein the reaction pressure in the column is at least atmospheric and wherein the sucrose polyester in the column reaction product comprises at least about 70% sucrose octaester.

* * * * *